United States Patent
Bernabei

[11] Patent Number: 6,149,634
[45] Date of Patent: Nov. 21, 2000

[54] COLLECTING BOTTLE FOR DERMABRASION TREATMENT

[75] Inventor: Gian Franco Bernabei, Florence, Italy

[73] Assignee: Mattioli Engineering Ltd., Florence, Italy

[21] Appl. No.: 09/168,680

[22] Filed: Oct. 9, 1998

Related U.S. Application Data

[62] Division of application No. 08/797,909, Feb. 10, 1997.

[30] Foreign Application Priority Data

May 10, 1996 [IT] Italy .................... F196A0108

[51] Int. Cl.[7] .................................................. A61M 1/00
[52] U.S. Cl. ........................................ 604/319; 606/131
[58] Field of Search ........................... 606/131; 604/313, 604/317, 319

[56] References Cited

U.S. PATENT DOCUMENTS

| | | | |
|---|---|---|---|
| 3,032,037 | 5/1962 | Huber | 604/319 |
| 3,608,553 | 9/1971 | Balamuth | 606/131 |
| 3,727,788 | 4/1973 | Holbrook | 604/319 |
| 3,773,211 | 11/1973 | Bridgman | 604/319 |
| 5,037,431 | 8/1991 | Summers et al. | 606/131 |
| 5,037,432 | 8/1991 | Molinari . | |
| 5,100,412 | 3/1992 | Rosso . | |
| 5,470,324 | 11/1995 | Cook et al. | 604/319 |
| 5,720,299 | 2/1998 | Theodoru | 604/317 |
| 5,741,237 | 4/1998 | Walker | 604/317 |
| 5,797,742 | 8/1998 | Fraker | 604/319 |
| 5,810,842 | 9/1998 | Di Fiore et al. | 606/131 |

FOREIGN PATENT DOCUMENTS

| | | | |
|---|---|---|---|
| 0564392 | 10/1993 | European Pat. Off. | 606/131 |
| 2712172 | 11/1993 | France | 606/131 |
| 67279 | 3/1985 | Italy | 606/131 |
| F194A0131 | 2/1996 | Italy . | |

*Primary Examiner*—Gene Mancene
*Assistant Examiner*—Eduardo C. Robert
*Attorney, Agent, or Firm*—Foley & Lardner

[57] ABSTRACT

A collecting bottle for a dermabrasion apparatus includes a first connection for connecting to a handle of the dermabrasion apparatus. The handle is used to apply dermabrading material to a patient and to output a mixture of dermabrading material and skin tissue along a path to the collecting bottle that includes the first connection. The collecting bottle includes a second connection for connecting to a vacuum pump. The vacuum pump provides a reverse pressure for drawing the mixture from the handle in a direction through the path and into the collecting bottle. The collecting bottle also includes a casing, and an air filter provided inside the casing for blocking the mixture collected in the collecting bottle from being drawn out of the collecting bottle and towards the vacuum pump via the second connection.

2 Claims, 2 Drawing Sheets

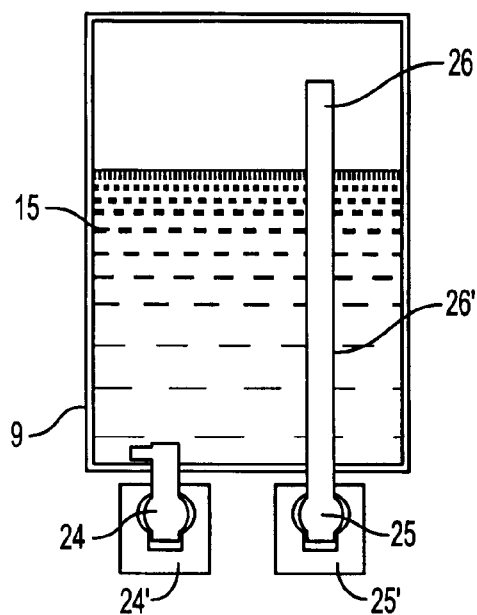
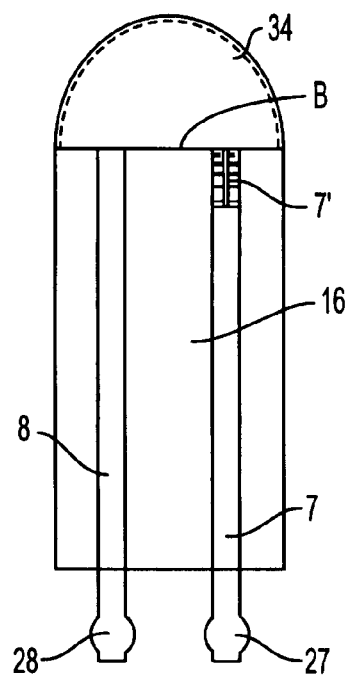
FIG. 4
FIG. 6
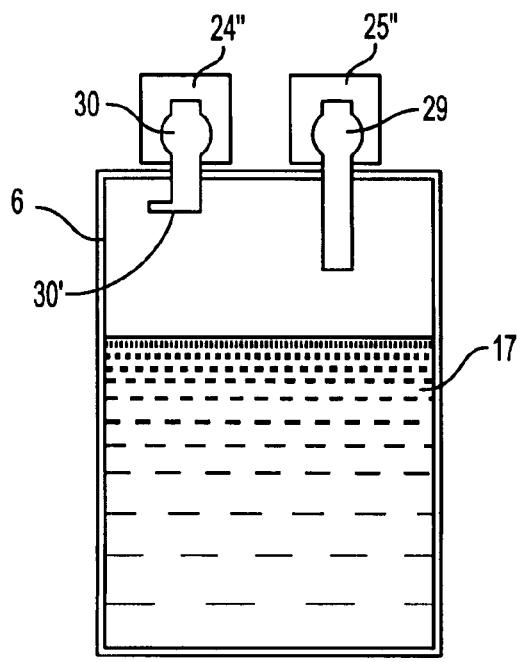
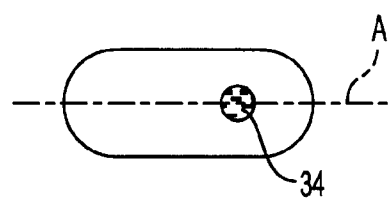
FIG. 5
FIG. 7
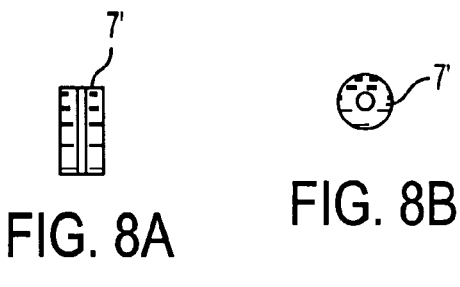
FIG. 8A
FIG. 8B

COLLECTING BOTTLE FOR DERMABRASION TREATMENT

This application is a divisional of application Ser. No. 08/797,909, filed Feb. 10, 1997.

FIELD OF THE INVENTION

The present invention relates to the field of the cosmetic and microsurgical treatments. In particular it refers to a microdermabrasion apparatus and to its most relevant components, operating by a pressurized flow of air and reducing substances, preferably corundum (Al2O3).

BACKGROUND OF THE INVENTION

Several technical solutions to produce a microdermabrasion apparatus are already known, all comprising vacuum means and/or pressurizing means which send a flow of air and reducing substances on a tissue portion to be treated and then remove from that portion the abraded particles. Such solutions have a drawback in that the sterility of the various components is not guaranteed, unless by complicated and expansive proceedings.

Italian patent application FI94A000131 describes a dermabrasion apparatus operating by a flow of reducing substances. The apparatus comprises a compressore, a vacuum pump, and three detachable onepiece components, a mixing bottle, a collecting bottle for the abraded particles and a contact handle to touch the tissue to be treated. Those parts are preferably made of glass or plastic material and can be easily sterilized.

However, such apparatus has some drawbacks due to the fact that the air pressurization is performed by a compressor placed inside the apparatus and therefore uneasy to be sterilized. Thus, during the treatment the compressor could be infected by bacteria which would be afterwards conveyed on the patient's skin by the pneumatic system. Furthermore, the above mentioned one piece components are sterilized after the apparatus has been used, but they do not guarantee a proper sterility when the apparatus performes succeeding treatments on different patients. A further drawback is that dangerous contaminations can occur when the mixing bottle is filled with new reducing substances or when the collecting bottle is cleaned of the abraded particles.

OBJECT OF THE INVENTION

A first object of the invention is to ensure the highest sterility of the apparatus components in whatever circumstances, also when sterilization means as UV ray or autoclave are not available. A further object of the invention is to obtain easy replaceable, low cost apparatus components.

SUMMARY OF THE INVENTION

The above objects have been reached according to the invention by a microdermabrasion apparatus provided with disposable sterilized components consisting of easily interchangeable one piece blocks. Such components comprehend an already filled mixing bottle containing the reducing substances, a collecting bottle for the abraded tissue particles, and a handle contacting the tissue during the treatment. All those components are manufactured and sealed in a sterilized environment. According to an embodiment of the invention the components are made of plastic material, preferably polycarbonate, in order to lower the costs, and to make them particularly suitable for disposable use. According to a still further embodiment of the invention, after manufacturing the components can be packed in sterilized packagings comprehending either a singol component or a multi-component kit. Thus, all the possible contamination risks are avoided, from the manufacturing to the use of the components. In order to avoid the contamination of the reducing substances, preferably corundum, with particles of the handle material abraded in the use, the portion of the handle most subjected to the abrasion effect is an abrasion proof block made of a suitable hard material, for example ceramics. According to a further embodiment of the invention, the source of pressurized air, or of an other suitable gas, is constituted by one disposable bottle or sterilized pressurized air. In such way sterility is guaranteed to all the apparatus components exposed to contamination risks, for each single treatment. A further advantage is due to the low cost production of such components.

DRAWINGS

Still further advantages will be evident from the following description and from the annexed drawings given as a non limitative example, in which:

FIG. 1 schematically shows the layout of the apparatus according to the invention;

FIG. 4 shows a preferred embodiment according to the invention of the mixing bottle filled with reducing substances;

FIG. 5 shows a preferred embodiment of the collecting bottle according to the invention;

FIG. 6 shows a preferred embodiment of the contacting handle according to the invention;

FIG. 7 shows a top view of the handle of FIG. 6;

FIGS. 8a, 8b show different views of the abrasion proof block of the handle of FIG. 6

DETAILED DESCRIPTION OF THE INVENTION

Figure 1:
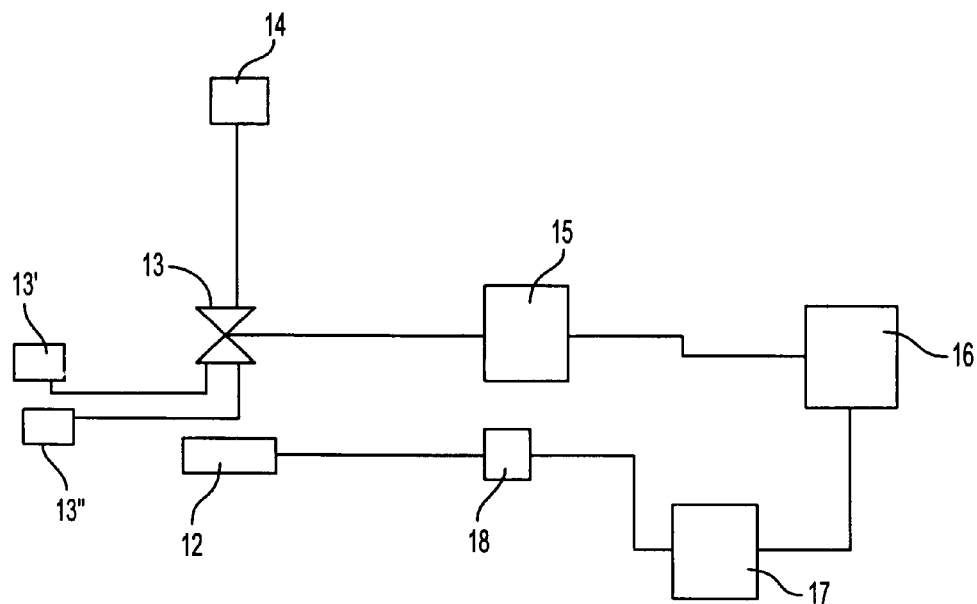

Referring to FIG. 13, a microdermabrasion apparatus 10 according to the invention comprises a carter 11 housing: a vacuum pump 12, a mixing bottle 15 containing the reducing substances and a bottle 17 to collect the reducing substances and the abraded tissue particles after use. Apparatus 10 is connected by a pneumatic system to an handle 16 intended to contact the tissue portion during the treatment. In the described embodiment it is also provided a valve 13 controlled by a switch 14, for example a treadle switch, able to switch the air inlet from two different sources 13', 13". The first source is a bottle of pressurized and sterilized air, and the second source is air at the environmental pressure. Downstream the bottle 17 and upstream the vacuum pump 12 it is also provided a filter 18 to stop possible small particles flowing accidentaly from the bottle 17.

Figures 2, 3:
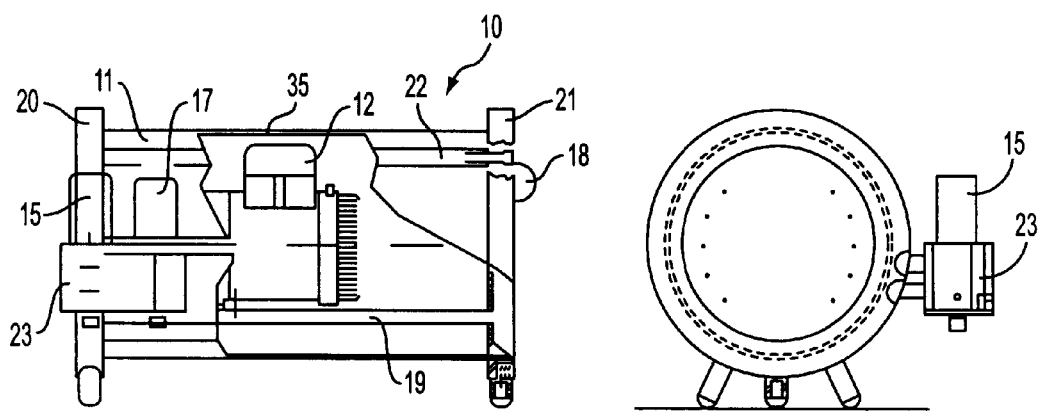
FIG. 2 shows a side view of the apparatus.
FIG. 3 shows a front view of the apparatus of FIG. 2.

In FIGS. 2, 3 it is illustrated a possible embodiment of the carter 11, constituted by a casing 35, preferably made of plexiglass, and a bar 19 supporting the vacuum pump 12, where a couple of lateral flanges 20, 21 are connected by threated tierod 22. Carter 11 includes also a cup 23, fixed to the flange 20, housing the mixing bottle 15 and the collecting bottle 17. Flange 21 holds the filter 18 placed immediately upstream the vacuum pump 12. Referring to FIG. 4 the mixing bottle 15 is a substantially cilindrical one piece block obtained, for example, by ultrasound welding following an orizzontal junction line 9. Mixing bottle 15 is provided with connection pipes 24, 25 connected respectively with valve 13, not shown in the drawings, and with the pneumatic duct leading to the handle 16 according to the scheme of FIG. 1. Pipe connection 25 extends into the bottle 15 with a suction tube 26 having a hole 26' near the bottom wall of bottle 15, through which the reducing substances are introduced into the pneumatic system.

According to the invention, the bottle 15 is filled with the corundum in an aseptic environment and thereafter is closed, preferably by welding, and then sealed by suitable plug 24' 25'. For example, each plugs 24', 25' can have a bottom rubber layer which is pierced by the extremities of corresponding connecting junctions of the cup 23 when the plugs are fitted into the cup. In such way the bottle 15 is connected with the valve 13 and with the downstream handle 16.

Referring to FIG. 6, handle 16 is constitued by a substantially cylindrical one piece block having the upper portion in shape of an hollow spherical cap. Handle 16 is provided with an inlet connection 27 corresponding to an inner tube 7 through which the air and the reducing substances enter into the spherical cap. After use, the reducing substances are removed from the spherical cap by a second tube 8 and a corresponding outlet connection 28. The handle spherical cap presents an opening 34 the rim of which defines the patient's tissue portion hit by the reducing substances ejected from tube 7.

According to the invention the upper end of tube 7, which is the part subjected to the highest abrasion, is provided with an insert block 7', shown in FIGS. 8a, 8b. Block 7' is a cylinder having an internal diameter smaller than the tube 7 diameter, so that in that point the flow area is smaller and the flow rate of the reducing substances increases. Block 7' is made of an hard material, preferably ceramics. In the described embodiment, handle 16 is constitued by two half parts symmetrical in respect of section A of FIG. 7 and manufactured by injection moulding, together with the corresponding half parts of tubes 7, 8. Before assembling, block 7' is inserted into the upper end portion of tube 7 and the spherical cap is put on so that the opening 34 corresponds to the block 7' position. After that the assembly is closed, for example by ultrasound welding according to section A and section B between the spherical cap and the cylindrical body. Alternatively, the spherical cap is welded to the lower cylindrical body obtained by a single injection moulding operation.

Referring to FIG. 5, it is described the collecting bottle 17, placed downstream handle 16 and upstream pump 12, according to the pneumatic system scheme of FIG. 1. Bottle 17 is constitued by a cylindrical hollow one piece block provided with two upper connections 29, 30, the first operating as inlet of the reducing substances from handle 16, the second as passage of the air aspirated by pump 12. Connection 30 is provided with an air filter 30' in order to avoid the passage of the used reducing substances and of tissue abraded particles towards the pump 12. In the described embodiment, bottle 17 is assembled by welding according to section 6, the upper portion comprehending connections 29,30. Immediately downstream the bottle 17 is placed a filter 18 intended to filter possible small particles passed through the filter 30' and conveyed towards pump 12. Advantageously, the connections of bottle 17 and handle 16 are provided with plugs similar to the already described plugs 24', 25' which are intended both to seal bottle 17 and handle 16 till they are first used, and to allow a quick connection to the pneumatic system. According to the invention, after manufacturing said bottle 15, 17 and handle 16 can be packaged, one by one or in a unique kit, in a sterilized packaging, possibly comprehending the needed connection tubes. Said one piece blocks constitue a kit of disposable components which allows to avoid the stages of filling with the reducing substances, cleaning of the abraded particles and of sterilization of the critical parts of the apparatus, which stages till now represented a drawback to the treatment safety and a further increasing on costs and time. It is also possible to fix an expiring time for the sterility condition of the blocks contained in said unique kit packaging, so that, according to such time, all the critical parts of the apparatus can be safety a quickly replaced thanks to the described sealing plugs of blocks 15, 16, 17. Said blocks can be made of any suitable plastic or vetrous material. Anyhow, policarbonate is preferred because it is a low cost material and is sterilizable by autoclave when a reuse of one or more components is needed. According to a furhter feature of the invention, the kit components present different colours in order to allow a better identification of their functions by the user.

What is claimed is:

1. A collecting bottle for use in dermabrasion, comprising:
   a first connection for connecting to a handle, the handle being configured to apply dermabrading material to a patient and to output a mixture of dermabrading material and skin tissue along a path that includes a first connection;
   a second connection for connecting to a vacuum pump, the vacuum pump being configured to provide a reverse pressure for drawing the mixture from the handle in a direction through the path and into the collecting bottle;
   a casing; and
   a filter provided inside the casing for blocking the mixture collected in the collecting bottle from being drawn out of the collecting bottle and towards the vacuum pump via the second connection,
   wherein the first connection, the second connection, and the casing are formed as a one-piece block, and
   wherein the filter is disposed in a direct path of the second connection,
   wherein the collecting bottle further comprises, as elements separate from the one-piece block;
      a first connection plug provided at an end portion of the first connection; and
      a second connection plug provided at an end portion of the second connection,
   wherein the first and second connection plugs are rubber stoppers that maintain an internal space within the casing to be protected from an external environment prior to respectively connecting the collecting bottle to the handle and to the vacuum pump via the first and second connections, and
   wherein the first and second connection plugs act to seal the inner space within the casing both prior to and after a dermabrasion process of the patient and during the dermabrasion process of the patient.

2. A collecting bottle bottle for use in dermabrasion, comprising:
   a first connection for connecting to a handle;
   a second connection for connecting to a pressurized unit;
   a casing; and
   a filter provided inside the casing for blocking contents collected in the collecting bottle from being drawn out of the collecting bottle and towards the pressurized unit via the second connection, wherein the first connection, the second connection, the casing and the filter are formed as a one-piece block, wherein the collecting bottle further comprises, as elements separate from the one-piece block;

a first connection plug provided at an end portion of the first connection; and a second connection plug provided at an end portion of the second connection, wherein the first and second connection plugs are rubber stoppers that maintain an internal space within the casing to be protected from an external environment prior to respectively connecting the collecting bottle to the handle and to the pressurized unit via the first and second connections, and wherein the first and second connection plugs act to seal the inner space within the casing both prior to and after a dermabrasion process of the patient and during the dermabrasion process of the patient.

\* \* \* \* \*